(12) United States Patent
Keen

(10) Patent No.: US 7,111,499 B2
(45) Date of Patent: Sep. 26, 2006

(54) VISCOMETER TUBE

(75) Inventor: Jeff A. Keen, Edmonton (CA)

(73) Assignee: The Fluid Life Corporation, Edmonton (CA)

( * ) Notice: Subject to any disclaimer, the term of this patent is extended or adjusted under 35 U.S.C. 154(b) by 0 days.

(21) Appl. No.: 10/987,026

(22) Filed: Nov. 12, 2004

(65) Prior Publication Data
US 2005/0132780 A1   Jun. 23, 2005

(30) Foreign Application Priority Data
Dec. 23, 2003   (CA) .................................... 2450483

(51) Int. Cl.
*G01N 11/04* (2006.01)
(52) U.S. Cl. .................................... 73/54.04; 73/54.01
(58) Field of Classification Search ............... 73/54.01, 73/54.04
See application file for complete search history.

(56) References Cited
U.S. PATENT DOCUMENTS

| | | | | |
|---|---|---|---|---|
| 2,343,061 A | * | 2/1944 | Irany | .................. 73/54.04 |
| 3,559,463 A | * | 2/1971 | Tovrog et al. | ............. 73/54.07 |
| 3,981,182 A | * | 9/1976 | Kossler et al. | ............. 73/54.08 |
| 5,756,883 A | | 5/1998 | Forbes | |
| 6,261,771 B1 | * | 7/2001 | Bohannon | ...................... 435/6 |

FOREIGN PATENT DOCUMENTS

CA   2145599   12/2001

* cited by examiner

*Primary Examiner*—Daniel S. Larkin
(74) *Attorney, Agent, or Firm*—Davis & Bujold, P.L.L.C.

(57) ABSTRACT

A viscometer tube includes a tubular body divided into three sections: an upper feed section, a lower capillary section and an intermediate transition section providing a transition between the upper feed section and the lower capillary section. Liquid flows from the upper feed section to the intermediate transition section and then to the lower capillary section. The upper feed section intersects the intermediate transition section either laterally or from below. An upper remote end of the intermediate transition section is open to atmosphere.

8 Claims, 4 Drawing Sheets

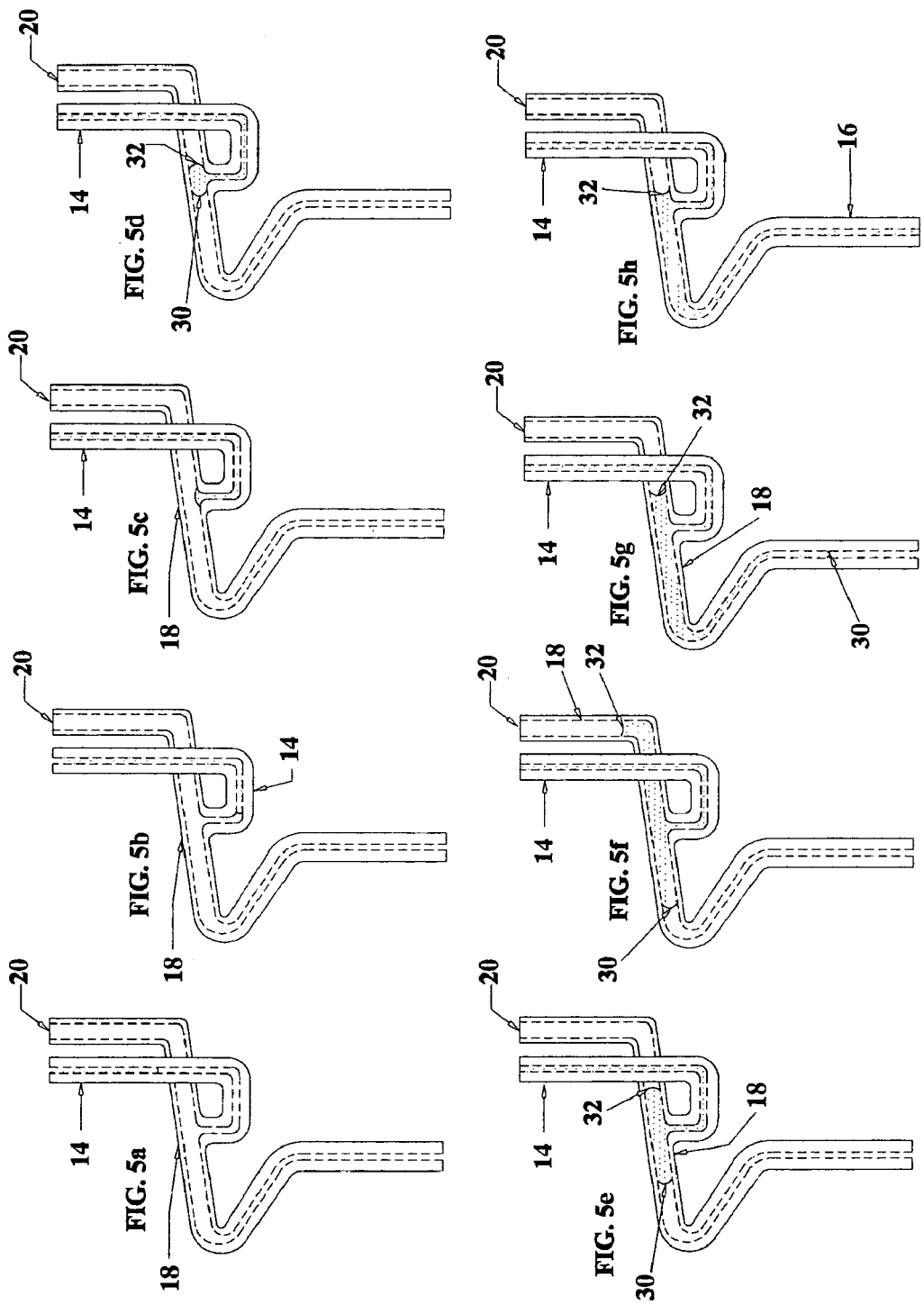

VISCOMETER TUBE

This application claims priority from Canadian patent application serial no. 2,450,483 filed Dec. 23, 2003.

FIELD OF THE INVENTION

The present invention relates to a configuration for a viscometer tube used to feed liquids into a viscometer.

BACKGROUND OF THE INVENTION

One of the key aspects for the accurate operation of a viscometer is the configuration of viscometer tube used. Although the feed of liquid into each viscometer tube is frequently automated, the flow of liquid in the tube when passing the sensors must be solely by force of gravity in order ensure an accurate reading.

SUMMARY OF THE INVENTION

What is required is a new viscometer tube configuration which is better suited for automated feed systems.

According to the present invention there is provided a viscometer tube which includes a tubular body divided into three sections: an upper feed section, a lower capillary section and an intermediate transition section providing a transition between the upper feed section and the lower capillary section. Liquid flows from the upper feed section to the intermediate transition section and then to the lower capillary section. The upper feed section intersects the intermediate transition section either laterally or from below. An upper remote end of the intermediate transition section is open to atmosphere.

With the viscometer tube, as described above, the upper remote end of the intermediate transition section is open to atmosphere during injection and measurement. The upper feed section intersecting the intermediate transition section from either laterally or below, permits two meniscus to form without air being trapped in the middle. The transition section becomes loaded with the sample, before any movement occurs. Once injection from the upper feed section is complete, liquid passes from the intermediate transition section into the lower capillary section solely by force of gravity. Once the teachings of the present invention are understood, various modifications can be added to further enhance the operation of the viscometer tube.

Although beneficial results may be obtained through use of the viscometer tube, as described above, it has been found that performance can be further improved when the upper feed section is generally "J" shaped and feeds into the intermediate transition section from below.

Although beneficial results may be obtained through use of the viscometer tube, as described above, it has been found that performance can be further improved when the intermediate transition section is inclined to initiate liquid flow.

Although beneficial results may be obtained through use of the viscometer tube, as described above, it has been found that performance can be further improved when the lower capillary section is straight. It is preferred that the lower capillary section has a first portion of a first internal diameter and a second portion of a second internal diameter, which is smaller than the first internal diameter.

Although beneficial results may be obtained through the use of the viscometer tube, as described above, the dwell time in the tube before the sensors must be also sufficient that the liquid can be heated to a predetermined temperature. When liquids are tested at different temperatures, the results of viscosity testing are not reliable. Even more beneficial results may, therefore, be obtained when the intermediate transition section defines a spiral to increase dwell time.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein:

FIG. 5a, 5b, 5c, 5d, 5e, 5f, 5g, 5h are detailed side elevation views, in section, of the first embodiment of viscometer tube shown in various stages of a liquid flow sequence.

DETAILED DESCRIPTION OF THE PREFERRED EMBODIMENT

Figure 3:
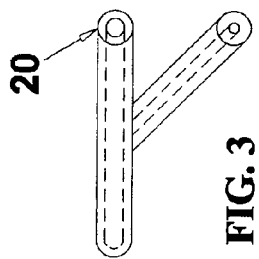
FIG. 3 is a top plan view, of the first embodiment of viscometer tube illustrated in FIG. 1.

The preferred embodiment, a viscometer tube generally identified by reference numeral 10, will now be described with reference to FIGS. 1 through 5.

Figure 4:
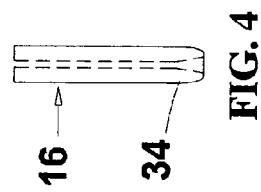
FIG. 4 is a detailed side elevation view, in section, of a remote end of the lower capillary section of the first embodiment of viscometer tube illustrated in FIG. 1.
Figure 2:
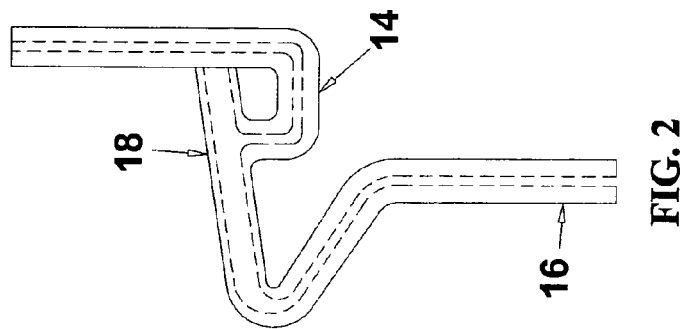
FIG. 2 is a detailed side elevation view, in section, of the upper feed section and intermediate transition section of the first embodiment of viscometer tube illustrated in FIG. 1.
Figure 1:
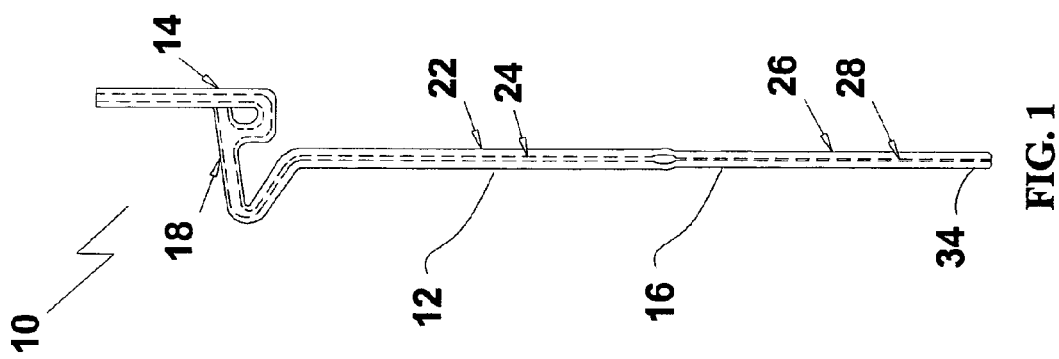
FIG. 1 is a side elevation view, in section, of a first embodiment of viscometer tube constructed in accordance with the teachings of the present invention.

Structure and Relationship of Parts:

Referring to FIG. 1, viscometer tube 10 has a tubular body 12 divided into three sections: an upper feed section 14, a lower capillary section 16 and an intermediate transition section 18. Intermediate transition section 18 provides a transition between upper feed section 14 and lower capillary section 16. The sections are arranged so that liquid flows sequentially from upper feed section 14 to intermediate transition section 18 and then to lower capillary section 16. Referring to FIG. 2, upper feed section 14 is generally "J" shaped and intersects intermediate transition section 18 from below. Referring to FIG. 3, an upper remote end 20 of intermediate transition section 18 is open to atmosphere. The remote end 20 may in fact be connected to a set of valves, and during injection and measurement remote end 20 is opened to atmosphere, where the valves would be used during cleaning. Referring to FIG. 2, intermediate transition section 18 is inclined to initiate gravity flow into lower capillary section 16. Referring to FIG. 1, lower capillary section 16 is maintained in a straight vertical orientation with a first portion 22 of a first internal diameter 24 and a second portion 26 of a second internal diameter 28 which is smaller than first internal diameter 24. Referring to FIG. 4, the remote end 34 of lower capillary section 16 is shown. The size of the remote end of the lower capillary section is of importance when the tube is mounted through the bottom of an oil bath tank in a compression fitting with [o] O-rings to ensure that the glass will fit and seal.

Operation:

Referring to FIG. 5a, the liquid being tested is pumped in through upper feed section 14. Referring to FIG. 5b, the liquid travels along the "J" shape of upper feed section 14. Referring to FIG. 5c, liquid enters intermediate transition section 18 from below. It will be appreciated, that somewhat similar results may be obtained by having the liquid enter through the side of intermediate transition section 18. Referring to FIG. 5d, two meniscus form, which are hereinafter identified by reference numerals 30 and 32. It is noteworthy that meniscus 30 and 32 can be formed repeatedly and consistently, without air being trapped between them. Referring to FIG. 5e, as more liquid is pumped in the distance between meniscus 30 and 32 grows, while the sample remains within intermediate transition section 18. Referring to FIG. 5f, at the point shown, the entire sample is in intermediate transition section 18 and pumping has ceased. Referring to FIG. 5g, the entry of air through upper remote end 20 of intermediate transition section 18, along with the incline of intermediate transition section 18, sets the sample in motion. Referring to FIG. 5h, the ample flows from intermediate transition section 18 into lower capillary section 16. Referring to FIG. 1, lower capillary section 16 is in a straight vertical orientation with first portion 22 of first internal diameter 24 and second portion 26 of second internal diameter 28, which is smaller than first internal diameter 24. The improved measurement accuracy by using differing diameters of capillary tube is known in the art and, for that reason, will not be further described.

Figure 6:
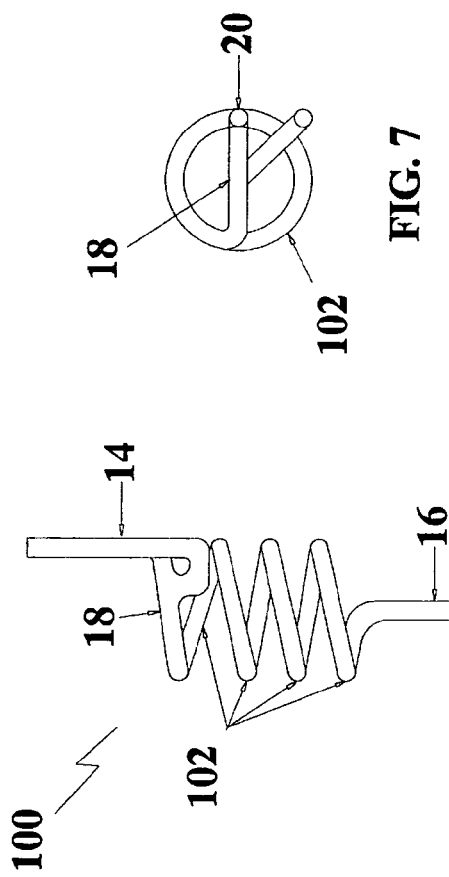
FIG. 6 is a side elevation view of a second embodiment of viscometer tube constructed in accordance with the teachings of the present invention.
Figure 7:
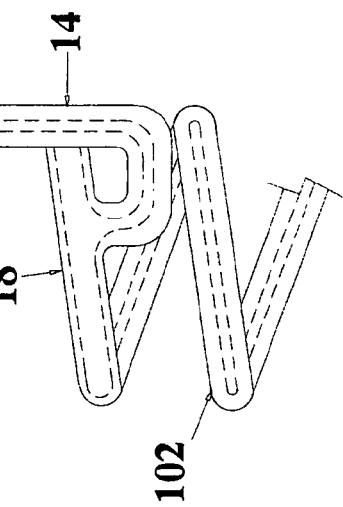
FIG. 7 is a top plan view of the second embodiment of viscometer tube illustrated in FIG. 6.
Figure 8:
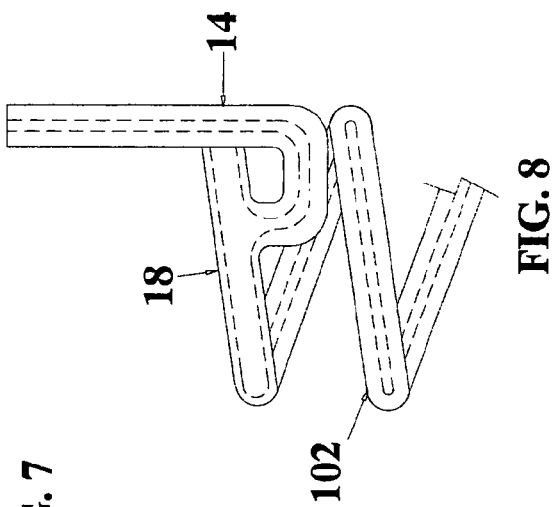
FIG. 8 is a detailed side elevation view, in section, of the second embodiment of viscometer tube illustrated in FIG. 6.
Figure 9:
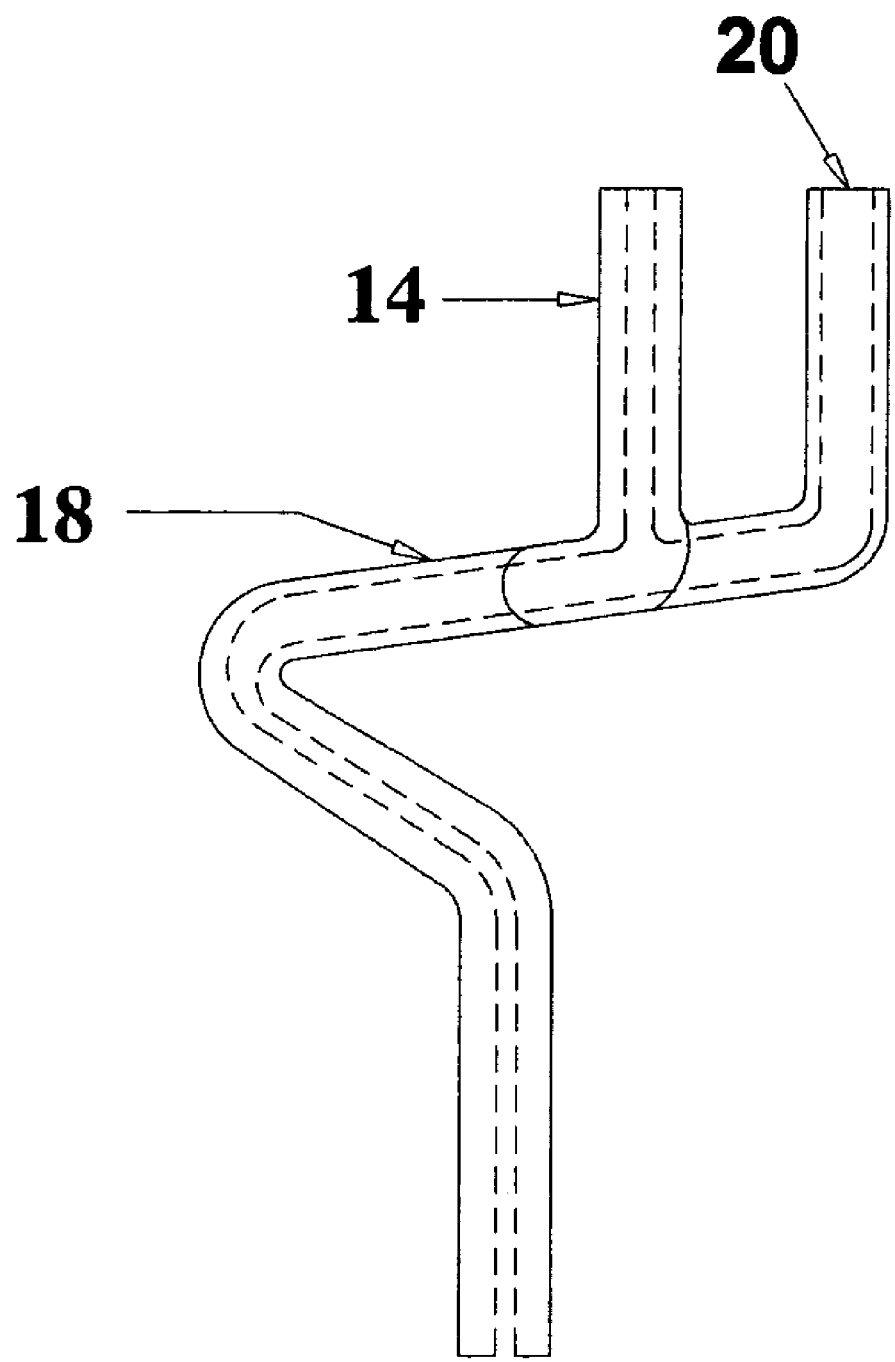
FIG. 9 is a detailed side elevation view, in section, of a further embodiment of viscometer tube constructed in accordance with the teachings of the present invention.

Variations:

A variation of the preferred embodiment will now be discussed with reference to FIGS. 6 through 8. There is illustrated a second embodiment of viscometer tube, generally identified by reference numeral 100. In most respects viscometer tube 100 is identical to viscometer tube 10. For that reason, identical reference numerals will be used to identify identical elements. However, in viscometer tube 100 an addition has been made to intermediate transition section 18. In this embodiment, intermediate transition section has added to it a spiral portion 102. Spiral portion 102 is intended to increase the dwell time of liquid within intermediate transition section 18. The purpose of increasing the dwell time is to permit the sample to be heated to a predetermined temperature prior to passing by gravity flow into lower capillary section 16. Viscosity changes with temperature. Therefore, in order to have consistent and repeatable results it is important with most liquids that measurements are always taken at the same temperature. It will be understood to persons skilled in the art the use of spiral portion alone, has utility even in the absence of the other aspects of the invention.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

The embodiments of the invention in which an exclusive property or privilege is claimed are defined as follows:

1. A viscometer tube, comprising:
   a tubular body divided into three sections: an upper feed section, a lower capillary section and an intermediate transition section providing a transition between the upper feed section and the lower capillary section, liquid flowing from the upper feed section to the intermediate transition section and then to the lower capillary section;
   the upper feed section intersecting the intermediate transition section either laterally or from below; and
   an upper remote end of the intermediate transition section being open to atmosphere.

2. The viscometer tube as defined in claim 1, wherein the upper feed section is generally "J" shaped and intersects the intermediate transition section from below.

3. The viscometer tube as defined in claim 1, wherein the intermediate transition section is inclined to initiate gravity flow.

4. The viscometer tube as defined in claim 3, wherein the intermediate transition section defines a spiral.

5. The viscometer tube as defined in claim 1, wherein the lower capillary section is straight.

6. The viscometer tube as defined in claim 5, wherein the lower capillary section has a first portion of a first internal diameter and a second portion of a second internal diameter, which is smaller than the first internal diameter.

7. A viscometer tube, comprising:
   a tubular body divided into three sections: an upper feed section, a lower capillary section and an intermediate transition section providing a transition between the upper feed section and the lower capillary sections, liquid flowing from the upper feed section to the intermediate transition section, and then to the lower capillary section;
   the upper feed section being "J" shaped and intersects the intermediate transition section from below; an upper remote end of the intermediate transition section being open to atmosphere;
   the intermediate transition section being inclined to initiate gravity flow; and
   the lower capillary section being straight with a first portion of a first internal diameter and a second portion of a second internal diameter, which is smaller than the first internal diameter.

8. The viscometer tube as defined in claim 7 wherein the intermediate transition section defines a spiral.

* * * * *